United States Patent [19]
Endo et al.

[11] Patent Number: 5,888,805
[45] Date of Patent: Mar. 30, 1999

[54] DETECTING APPARATUS FOR MONITORING CULTURE BROTH IN BIO-REACTOR

[75] Inventors: Isao Endo; Teruyuki Nagamune, both of Wako; Kozo Inoue; Kinichi Kawamura, both of Tokyo, all of Japan

[73] Assignees: Rikagaku Kenkyusho, Saitama-ken; Komatsugawa Chemical Engineering Co., Ltd., Tokyo, both of Japan

[21] Appl. No.: 864,398

[22] Filed: May 28, 1997

[30] Foreign Application Priority Data

May 30, 1996 [JP] Japan ................................. 8-137256

[51] Int. Cl.⁶ ................................................ C12M 3/00
[52] U.S. Cl. ............................... 435/287.1; 435/288.7; 435/289.1; 435/817; 422/82.04; 422/82.12
[58] Field of Search .................. 435/286.1, 287.1, 435/288.7, 289.1, 817; 422/82.04, 82.06, 82.12; 73/866.5; 356/39, 41, 317

[56] References Cited

U.S. PATENT DOCUMENTS

| 4,315,990 | 2/1982 | Sheets .................................... 435/291 |
| 4,579,631 | 4/1986 | Ishikawa et al. ........................ 204/1 T |
| 4,680,267 | 7/1987 | Eppstein et al. ........................ 435/289 |

*Primary Examiner*—David A. Redding
*Attorney, Agent, or Firm*—Henderson & Sturm

[57] ABSTRACT

A detecting apparatus is disclosed, that comprises plural measurement devices with respective sensors and a support for holding the measurement devices in such a manner that the individual sensors contact a culture broth, the turbidity, dissolved oxygen, dissolved carbon dioxide the temperature, pH, and so forth of the culture broth being obtained by the measurement devices.

5 Claims, 2 Drawing Sheets

DETECTING APPARATUS FOR MONITORING CULTURE BROTH IN BIO-REACTOR

BACKGROUND OF THE INVENTION

1. Field of the Invention

The present invention relates to a detecting apparatus for monitoring a culture broth of bacteria, a yeast, a tissue of an animal/plant, a cell thereof, or the like cultivated in a bio-reactor.

2. Description of the Related Art

Conventionally, bacteria, a yeast, a tissue of an animal/plant, a cell thereof, and so forth are cultivated by bio-reactors whose internal environments are properly controlled. The turbidity, dissolved oxygen, dissolved carbon dioxide, the temperature, pH, and so forth of the culture broth in such a bio-reactor are detected so as to monitor the physiological activity of an organism in the culture broth.

In a conventional bio-reactor, to detect the turbidity, dissolved oxygen, dissolved carbon dioxide, the temperature, pH, and so forth of the culture broth, plural opening portions are formed on the side wall of the bio-reactor. Measurement devices that detect these measurement items are disposed in the bio-reactor through these opening portions.

However, in such a related art reference, the opening portions for the measurement devices disposed in the bio-reactor cause foreign matters such as various bacteria and impurities to enter the inside of the bio-reactor, resulting in contaminating the inside of the bio-reactor. In addition, plural of measurement devices disposed in the bio-reactor disorder the liquid flow, resulting in adversely affecting the cultivation of microorganisms.

SUMMARY OF THE INVENTION

The present invention is made from the above-described point of view. An object of the present invention is to provide a detecting apparatus that suppresses foreign matters from entering a bio-reactor and reducing the disorder of the liquid flow therein.

The present invention is a detecting apparatus for monitoring a culture broth in a bio-reactor, comprising plural measurement devices with respective sensors and a holding means for holding said measurement devices in such a manner that the individual sensors contact the culture broth.

According to the present invention, with only one opening portion formed on the side wall of the bio-reactor, a block of measurement devices can be disposed. Thus, in addition to suppressing foreign matters from entering the inside of the bio-reactor, the detecting apparatus can reduce the disorder of liquid flow in the bio-reactor. Moreover, the block of measurement devices can be easily handled and thereby the maintainability thereof can be improved.

According to the present invention, since the individual measurement devices are compactly structured, output signals thereof are designed not to interfere with each other.

These and other objects, features and advantages of the present invention will become more apparent in light of the following detailed description of the best mode embodiment thereof, as illustrated in the accompanying drawings.

DESCRIPTION OF PREFERRED EMBODIMENTS

Figure 1:
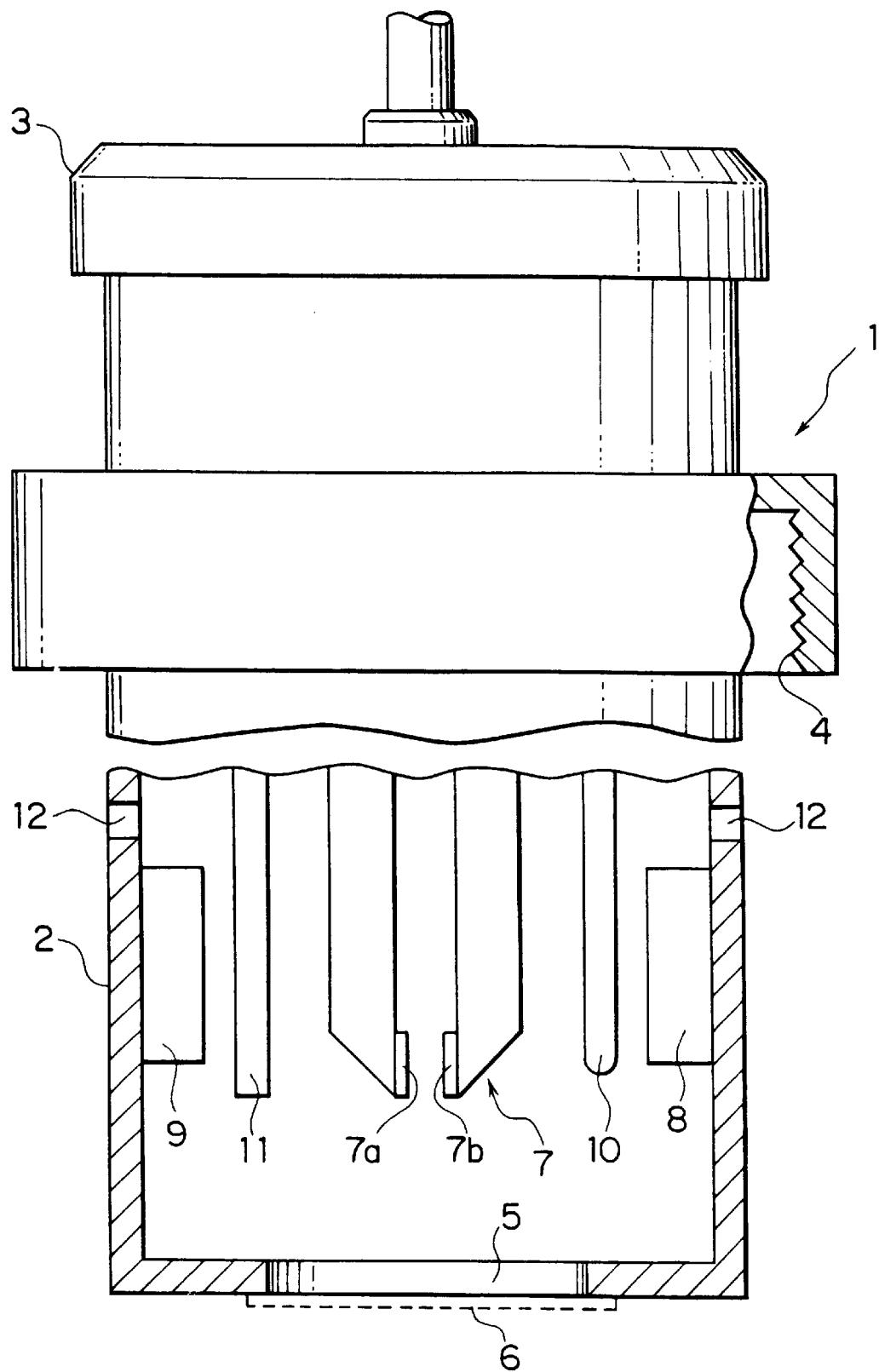
FIG. 1 is a partially exploded view showing principal portions of a detecting apparatus according to an embodiment of the present invention.

FIG. 1 is a partially exploded view showing principal portions of a detecting apparatus according to an embodiment of the present invention. Referring to FIG. 1, the detecting apparatus 1 according to the embodiment has a hollow cylindrical housing 2. A cap 3 is threaded with a top portion of the housing 2. As will be described later, a screw 4 is formed below the cap 3 so as to secure the detecting apparatus 1 to the side wall of the bio-reactor. An opening portion 5 for supplying a culture broth in the bio-reactor to the inside of the housing 2 is formed at a bottom portion of the housing 2. A mesh 6 is disposed in the opening portion 5. The mesh 6 prevents bubbles from entering the inside of the housing 2.

At a center portion of the housing 2, a turbidity detector 7 is disposed. The turbidity detector 7 has a light emitting portion 7a and a light receiving portion 7b. The light emitting portion 7a emits light of for example a semiconductor laser diode (not shown). The light receiving portion 7b receives the light emitted from the light emitting portion 7a and guides it to a semiconductor photodiode (not shown). The turbidity of the solution that is present between the light emitting portion 7a and the light receiving portion 7b is detected corresponding to the transmittance of the light of the solution.

A dissolved oxygen detector 8 and a dissolved carbon dioxide detector 9 are disposed on the inner wall of the housing 2. A temperature detector 10 is disposed between the turbidity detector 7 and the dissolved oxygen detector 8. A pH detector 11 is disposed between the turbidity detector 7 and the dissolved carbon dioxide detector 9. Signal lines of the detectors 7 to 11 vertically extend to an upper portion of the cap 3.

Plural holes 12 are formed in the side wall of the housing 2 so as to discharge the solution from the housing 2.

Figure 2:
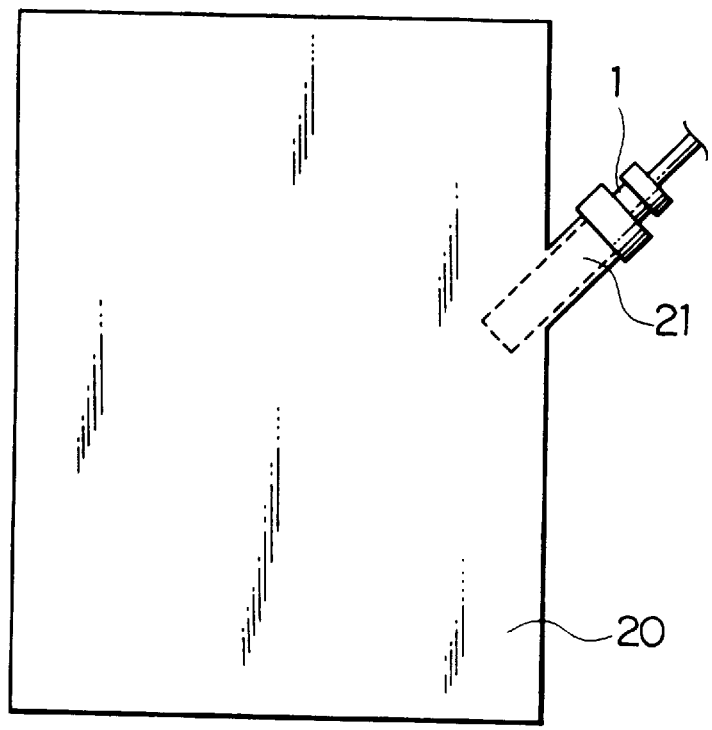
FIG. 2 is a schematic diagram showing the state of which the detecting apparatus shown in FIG. 1 is disposed in a bio-reactor.

As shown in FIG. 2, the detecting apparatus 1 is formed in a vessel shape. The detecting apparatus 1 is disposed in a bio-reactor 20 where bacteria, a yeast, a tissue of an animal/plant, a cell thereof, or the like is cultivated. In other words, the detecting apparatus 1 is disposed in a cylindrical opening portion 21 that protrudes from the side wall of the bio-reactor 20 with an angle in such a manner that a tip portion of the detecting apparatus 1 is soaked in the culture broth of the bio-reactor 20. The detecting apparatus 1 is secured by threading the screw 4 shown in FIG. 1 to a mate screw (not shown) formed outside the opening portion 21.

By measuring the turbidity, dissolved oxygen, dissolved carbon dioxide, the temperature, pH, and so forth of the culture broth in the bio-reactor 20 with the detecting apparatus 1, the physiological activity of an organism in the culture broth is monitored.

As described above, in the detecting apparatus 1 according to the embodiment, since the turbidity detector 7, the dissolved oxygen detector 8, the dissolved carbon dioxide detector 9, the temperature detector 10, and the pH detector 11 are integrally structured, they can be disposed in the bio-reactor 20 with only one opening portion 21.

Thus, with the detecting apparatus 1 according to the embodiment, foreign matters such as various bacteria and impurities can be suppressed from entering the inside of the bio-reactor. In addition, the disorder of the liquid flow in the bio-reactor 20 can be reduced. Moreover, since the detecting devices 7 to 11 can be easily handled (for example, they can be easily mounted and dismounted), the maintainability thereof is improved.

As described above, with the detecting apparatus according to the present invention, foreign matters can be suppressed from entering the inside of the bio-reactor and the disorder of the liquid flow in the bio-reactor can be reduced in comparison with the related art reference.

Although the present invention has been shown and described with respect to the best mode embodiment thereof, it should be understood by those skilled in the art that the foregoing and various other changes, omissions, and additions in the form and detail thereof may be made therein without departing from the spirit and scope of the present invention.

What is claimed is:

1. A detecting apparatus for monitoring a culture broth in a bio-reactor, comprising:

plural measurement devices with respective individual sensors, a housing for covering said measurement devices having at least one passage for the culture broth; and a holding means for holding said measurement devices in such a manner that the individual sensors contact the culture broth.

2. The detecting apparatus as set forth in claim 1, wherein said measurement devices contain at least one device selected from the group consisting of a turbidity detector, a dissolved oxygen detector, a dissolved carbon dioxide detector, a thermometer, and a pH detector.

3. The detecting apparatus as set forth in claim 1, wherein said housing is hollow and said at least one passage comprises an opening portion.

4. The detecting apparatus as set forth in claim 3, wherein the opening portion of said housing has a mesh for preventing bubbles from entering the inside of said housing.

5. A detecting apparatus for monitoring a culture broth in a bio-reactor, comprising:

plural measurement devices with respective sensors;

a hollow housing for said measurement devices having at least one passage comprising an opening portion through which the culture broth passes; and a holding means for holding said measurement devices in such a manner that the sensors contact the culture broth.

* * * * *